(12) United States Patent
Ide et al.

(10) Patent No.: US 10,398,297 B2
(45) Date of Patent: Sep. 3, 2019

(54) ANTIFOGGING DEVICE AND ENDOSCOPE DEVICE

(71) Applicant: OLYMPUS CORPORATION, Tokyo (JP)

(72) Inventors: Takayuki Ide, Akishima (JP); Yuta Sugiyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 253 days.

(21) Appl. No.: 15/446,445

(22) Filed: Mar. 1, 2017

(65) Prior Publication Data
US 2017/0172401 A1 Jun. 22, 2017

Related U.S. Application Data

(63) Continuation of application No. PCT/JP2014/076112, filed on Sep. 30, 2014.

(51) Int. Cl.
*A61B 1/12* (2006.01)
*A61B 1/00* (2006.01)
(Continued)

(52) U.S. Cl.
CPC .............. *A61B 1/127* (2013.01); *A61B 1/00* (2013.01); *A61B 1/0002* (2013.01);
(Continued)

(58) Field of Classification Search
CPC ..... A61B 1/127; A61B 1/128; A61B 1/00131; A61B 1/00057; A61B 1/0002; A61B 1/00006; A61B 1/00
(Continued)

(56) References Cited

U.S. PATENT DOCUMENTS 8,449,458 B2 * 5/2013 Shimizu ............. A61B 1/00032
600/160
9,561,070 B2 * 2/2017 Brotz ................. A61B 18/1206
(Continued)

FOREIGN PATENT DOCUMENTS

JP 2002291684 A * 10/2002 ........... A61B 1/0008
JP 2003-334157 A 11/2003
(Continued)

OTHER PUBLICATIONS

The Penguin Dictionary of Physics, 2000, Penguin books, p. 441 (Year: 2000).*
(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An antifogging device includes: an optical system having one or a plurality of optical members including at least an objective lens; a hollow casing in which the optical system is stored; a heater configured to generate heat according to supplied power to heat a hollow space in the casing; a temperature sensor configured to detect temperature of the hollow space; a temperature controller configured to estimate temperature difference between the temperature detected by the temperature sensor and temperature of the optical member, based on a power value of the supplied power; and an overall controller configured to control the heater based on the temperature difference estimated by the temperature controller.

8 Claims, 10 Drawing Sheets

(51) Int. Cl.
*A61B 1/05* (2006.01)
*A61B 1/06* (2006.01)

(52) U.S. Cl.
CPC ...... *A61B 1/00006* (2013.01); *A61B 1/00057* (2013.01); *A61B 1/00195* (2013.01); *A61B 1/051* (2013.01); *A61B 1/0684* (2013.01); *A61B 1/128* (2013.01)

(58) Field of Classification Search
USPC .................................................. 600/169, 118
See application file for complete search history.

(56) References Cited

U.S. PATENT DOCUMENTS

| | | | | |
|---|---|---|---|---|
| 2007/0149856 A1* | 6/2007 | Segawa | ............... | A61B 1/051 600/169 |
| 2008/0076087 A1* | 3/2008 | Horie | ............... | G02B 27/0006 433/29 |
| 2010/0168521 A1* | 7/2010 | Acha Gandarias | .. | A61B 1/0008 600/188 |
| 2014/0276766 A1* | 9/2014 | Brotz | ............... | A61B 18/1206 606/34 |
| 2014/0330266 A1* | 11/2014 | Thompson | ......... | A61B 18/1206 606/34 |
| 2015/0088125 A1* | 3/2015 | Wham | ............... | A61B 18/1233 606/40 |
| 2015/0238072 A1* | 8/2015 | Makmel | ............... | A61B 1/127 219/221 |
| 2015/0297070 A1* | 10/2015 | Ide | ............... | A61B 1/0008 600/103 |
| 2016/0345814 A1* | 12/2016 | Sidar | ............... | A61B 1/128 |

FOREIGN PATENT DOCUMENTS

| | | | | |
|---|---|---|---|---|
| JP | 2007-175230 A | | 7/2007 | |
| JP | 2009-148446 A | | 7/2009 | |
| JP | 2009261830 A | * | 11/2009 | ......... A61B 1/00096 |

OTHER PUBLICATIONS

International Search Report dated Jan. 13, 2015 issued in PCT/JP2014/076112.

* cited by examiner

ANTIFOGGING DEVICE AND ENDOSCOPE DEVICE

CROSS REFERENCES TO RELATED APPLICATIONS

This application is a continuation of PCT international application Ser. No. PCT/JP2014/076112, filed on Sep. 30, 2014 which designates the United States, incorporated herein by reference.

BACKGROUND

1. Technical Field

The disclosure relates to an antifogging device for preventing fogging of an objective lens. The disclosure also relates to an endoscope device having the antifogging device and configured to be introduced into a living body to acquire images in the living body.

2. Related Art

In a medical field, an endoscope device is conventionally used for observing an organ of a subject such as a patient. The endoscope device includes an insertion portion inserted into a body cavity of the subject, an imaging unit provided on a distal end of the insertion portion which takes an in-vivo image, and a display unit capable of displaying the in-vivo image taken by the imaging unit. When acquiring the in-vivo image by using the endoscope device, the insertion portion is inserted into the body cavity of the subject while emitting predetermined illumination light from the distal end of the insertion portion to take an image by the imaging unit.

The imaging unit includes an image sensor and an optical system including one or a plurality of optical members such as an objective lens which condenses outside light to form an image on the image sensor. Out of the optical system, the optical member on the most distal end (herein, it is described as the objective lens) is provided on the distal end of the insertion portion with a partial surface exposed to outside. Therefore, a surface of the objective lens might be fogged due to change in temperature (for example, change from 20° C. to 37° C.) in an environment when the insertion portion is inserted into a body from outside the body of the subject, for example. There is a problem that a clear in-vivo image cannot be acquired when the surface of the objective lens is fogged.

The endoscope device provided with a heating light guide which emits light for heating based on a detection result of a temperature sensor provided on the distal end of the insertion portion provided separate from an illuminating light guide which illuminates an imaging area by the imaging unit is disclosed as technology of inhibiting fogging of the surface of the objective lens (for example, refer to JP 2003-334157 A).

SUMMARY

In some embodiments, an antifogging device includes: an optical system having one or a plurality of optical members including at least an objective lens; a hollow casing in which the optical system is stored; a heater configured to generate heat according to supplied power to heat a hollow space in the casing; a temperature sensor configured to detect temperature of the hollow space; a temperature controller configured to estimate temperature difference between the temperature detected by the temperature sensor and temperature of the optical member, based on a power value of the supplied power; and an overall controller configured to control the heater based on the temperature difference estimated by the temperature controller.

In some embodiments, an endoscope device includes: an insertion portion having an imaging optical system including one or a plurality of optical members including at least an objective lens, an image sensor configured to capture a formed image transmitted through the imaging optical system, a hollow casing in which the imaging optical system and the image sensor are stored, a heater configured to generate heat according to supplied power to heat a hollow space in the casing, and a temperature sensor configured to detect temperature of the hollow space; a temperature controller configured to estimate, based on a power value of the supplied power, temperature difference between the temperature detected by the temperature sensor and temperature of an optical member among the one or the plurality of optical members of the imaging optical system, the optical member being located on a most distal end of the insertion portion; and an overall controller configured to control the heater based on the temperature difference estimated by the temperature controller.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter, referred to as "embodiment(s)") will be hereinafter described. In the embodiments, a medical endoscope device including an antifogging device according to the present invention which takes an image in a body cavity of a subject such as a patient to display is described. The present invention is not limited by the embodiment. The same reference signs are used to designate the same elements throughout the drawings.

First Embodiment

Figure 1:
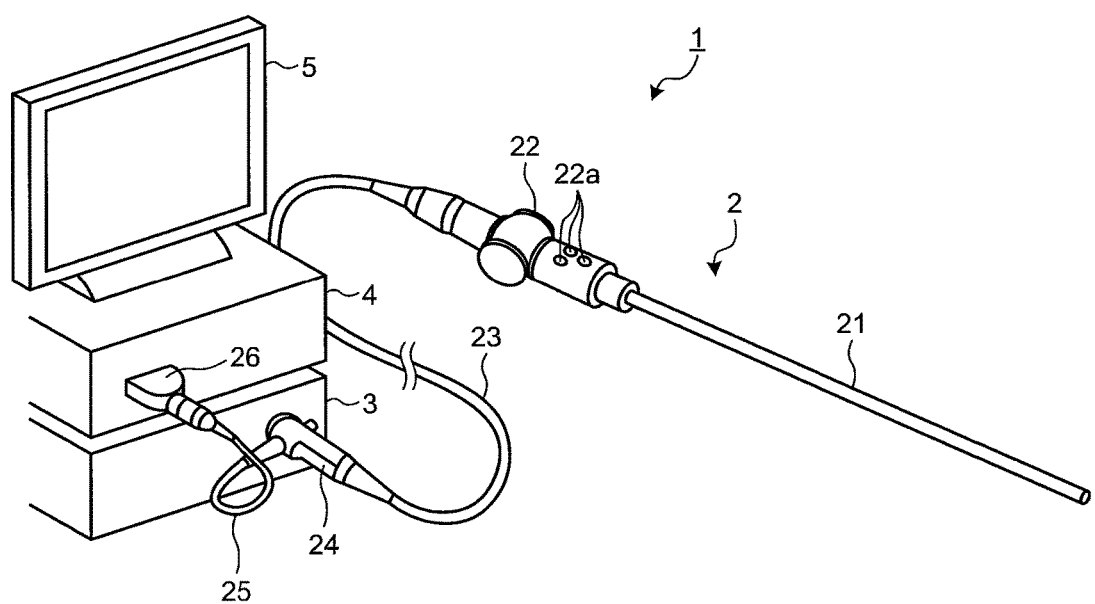
FIG. 1 is a schematic view illustrating a configuration of an endoscope device according to a first embodiment of the present invention.
Figure 2:
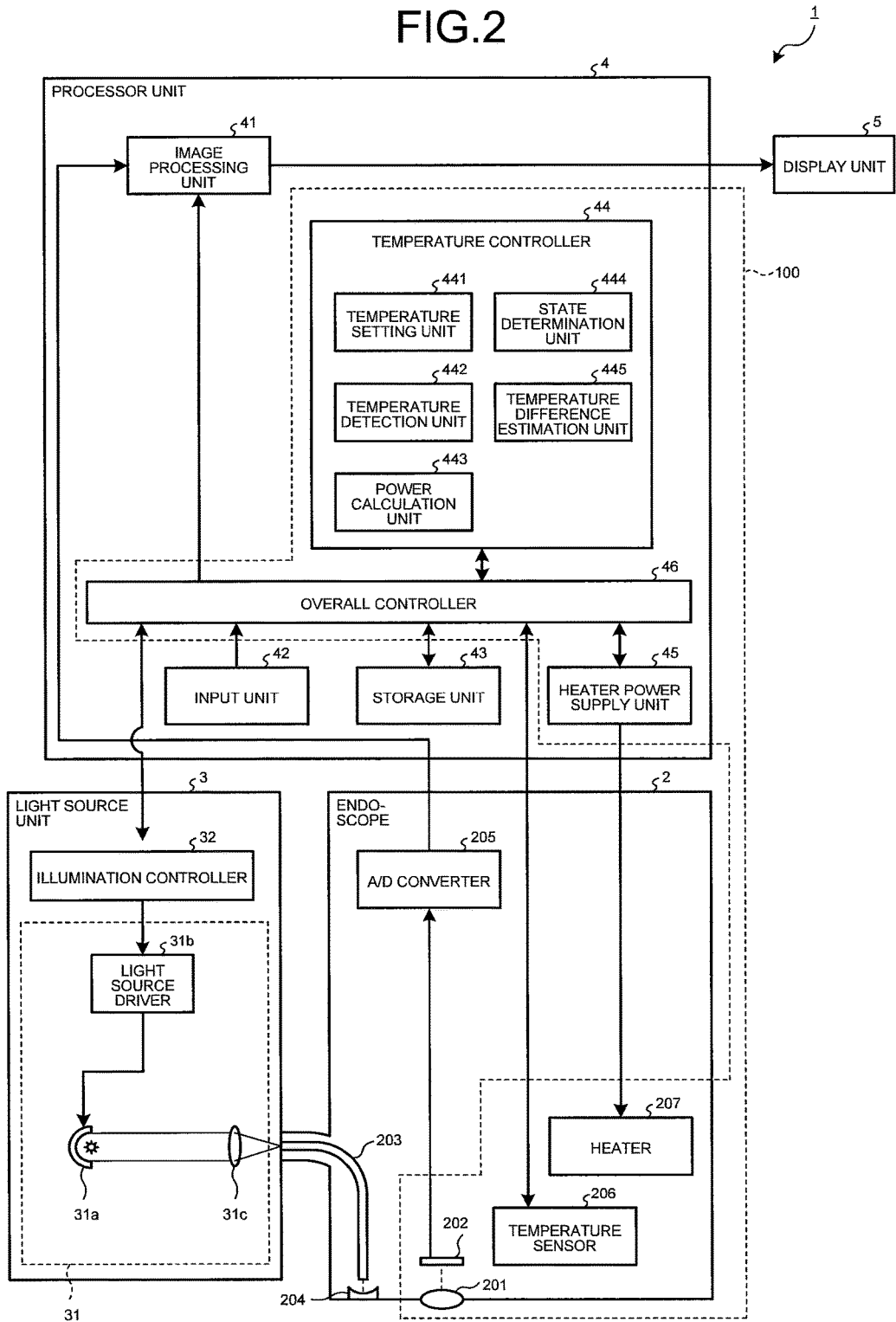
FIG. 2 is a schematic diagram illustrating the schematic configuration of the endoscope device according to the first embodiment of the present invention.

FIG. 1 is a schematic view illustrating a configuration of an endoscope device according to a first embodiment of the present invention. FIG. 2 is a schematic diagram illustrating the schematic configuration of the endoscope device according to the first embodiment. An endoscope device 1 illustrated in FIGS. 1 and 2 is provided with an endoscope 2 which takes an in-vivo image of an observed region with an insertion portion 21 inserted into a body cavity of a subject to generate an electric signal, a light source unit 3 which generates illumination light emitted from a distal end of the endoscope 2, a processor unit 4 which performs overall control of an entire endoscope device 1, and a display unit 5 which displays the in-vivo image on which the processor unit 4 performs image processing. In the first embodiment, it is described supposing that the endoscope 2 is a rigid scope inserted into an abdominal cavity of the subject to be used in laparoscopic surgery (surgery using endoscope) and the like.

The endoscope 2 is provided with an elongated insertion portion 21, an operating unit 22 connected to a proximal end side of the insertion portion 21 which accepts an input of various operation signals, a universal code 23 extending in a direction different from a direction in which the insertion portion 21 extends from the operating unit 22 in which various cables connected to the light source unit 3 and the processor unit 4 are embedded, a light source connector 24 provided on an end on a side different from a side connected to the operating unit 22 of the universal code 23 connected to the light source unit 3, an electric cable 25 extending from the light source connector 24, and an electric connector 26 provided on an end on a side different from a side connected to the light source connector 24 of the electric cable 25 connected to the processor unit 4.

The operating unit 22 includes a plurality of switches 22a which inputs a command signal for allowing the light source unit 3 to perform switching operation of the illumination light and an operation command signal of an external device connected to the processor unit 4.

The universal code 23 at least includes a light guide 203 and a cable assembly formed of one or a plurality of signal lines embedded therein. The cable assembly being the signal line which transmits and receives the signal between the endoscope 2 and the light source unit 3 and processor unit 4 includes the signal line for transmitting and receiving setting data, the signal line for transmitting and receiving an image signal and the like.

As illustrated in FIG. 2, the endoscope 2 is provided with an imaging optical system 201, an image sensor 202, the light guide 203, an illumination lens 204, an A/D converter 205, a temperature sensor 206, and a heater (heating member) 207.

The imaging optical system 201 at least includes an objective lens provided on a distal end of the insertion portion which condenses light from the observed region. The imaging optical system 201 is formed of one or a plurality of lenses as needed. The imaging optical system 201 may also be provided with an optical zooming mechanism which changes an angle of view and a focusing mechanism which changes a focal point. Although it is described that a part of a surface of the objective lens is exposed in the first embodiment, it is also possible that cover glass and the like is provided on a distal end thereof and a part of a surface of the cover glass is exposed. In the present invention, a member a surface of which is exposed from the distal end is an optical member.

The image sensor 202 provided so as to be perpendicular to an optical axis of the imaging optical system 201 performs photoelectric conversion on an image of the light formed by the imaging optical system 201 to generate the electric signal. The image sensor 202 is realized by using a charge coupled device (CCD) image sensor, a complementary metal oxide semiconductor (CMOS) image sensor and the like.

Herein, the image sensor 202 and the imaging optical system 201 are stored in a scope frame (casing) in which a hollow space is formed; in this embodiment, an objective lens frame 212 to be described later corresponds to the scope frame (casing).

The light guide 203 formed of a glass fiber and the like serves as a light guide path of the light emitted by the light source unit 3. In the first embodiment, two glass fibers are used.

The illumination lens 204 provided on a distal end of the light guide 203 diffuses the light guided by the light guide 203 to emit out of the insertion portion 21.

The A/D converter 205 performs A/D conversion on the electric signal generated by the image sensor 202 and outputs the converted electric signal to the processor unit 4.

The temperature sensor 206 provided in a neighboring area of the imaging optical system 201 detects temperature of an arrangement area (area to be detected) in which an objective lens 212a is arranged in the objective lens frame 212 to be described later. The temperature sensor 206 is realized by using a sheet-shaped thermoelectric couple, for example. Specifically, the temperature sensor 206 outputs a detection signal as electromotive force (thermal electromotive force) generated due to temperature difference between a reference junction and a temperature measuring junction. It is also possible that the temperature sensor 206 detects a resistance value and outputs the detected resistance value as the detection signal.

The heater 207 being a chip-shaped heater formed of a plurality of sections or a sheet-shaped heater formed of resistance drawn on one substrate by printing and the like realized by using a ceramic heater, a film heater and the like, for example, generates heat according to power supplied from the processor unit 4 under control of the processor unit 4.

The endoscope 2 may also include a storage unit which stores various programs for operating the endoscope 2 and data including various parameters required for the operation of the endoscope 2, identification information of the endoscope 2 and the like. The storage unit realized by using a flash memory and the like stores the identification information such as specific information (ID), a year model, specification information, and a transmission system of the endoscope 2.

Figure 3:
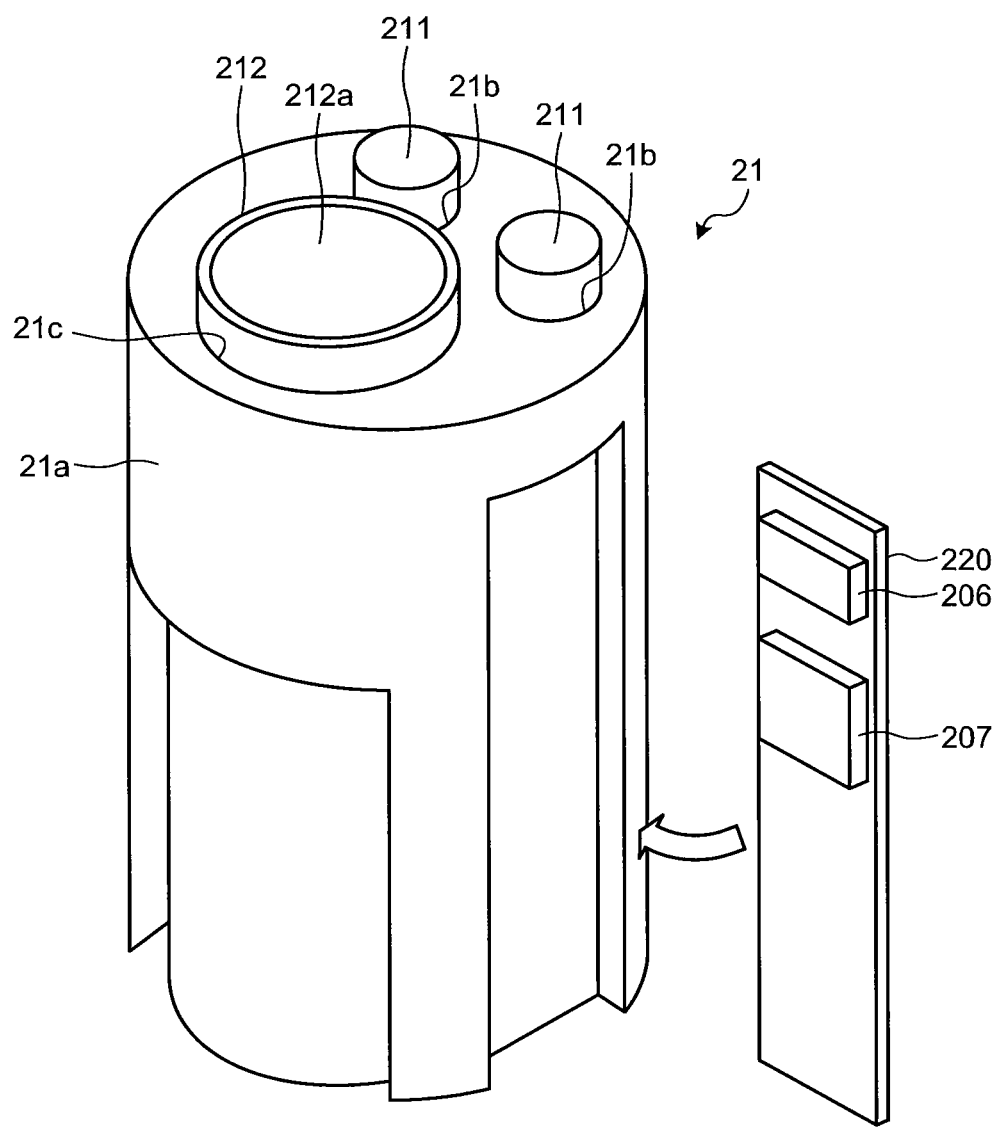
FIG. 3 is a schematic diagram illustrating an internal configuration of a distal end of an insertion portion of an endoscope according to the first embodiment of the present invention.

FIG. 3 is a schematic diagram illustrating an internal configuration of the distal end of the insertion portion of the endoscope according to the first embodiment. Two light guides 211 each of which holds the glass fiber (light guide 203) and the objective lens frame 212 which holds the imaging optical system 201 including the objective lens 212a and the image sensor 202 are formed on the distal end of the insertion portion 21, and a frame member 21a having a cylindrical shape with a bottom attached to the distal end of the insertion portion 21 is provided thereon. The frame member 21a is attached such that the bottom thereof is located on the distal end of the insertion portion 21. Insertion holes 21b and 21c through which the light guide 211 and the objective lens frame 212 are inserted, respectively, are provided on the bottom. The insertion portion 21 is covered with an exterior member (for example, a member formed of a metal material) not illustrated in a state in which the above-described frame member 21a is attached to the distal end thereof.

A wiring substrate 220 which holds the temperature sensor 206 and the heater 207 attached to a side surface of the frame member 21a is provided on the frame member 21a. The wiring substrate 220 is attached to the frame member 21a such that the temperature sensor 206 and the heater 207 are arranged on an inner peripheral side of the frame member 21a. The temperature sensor 206 and the heater 207 are arranged in the vicinity of the objective lens frame 212 when being attached to the frame member 21a. The temperature sensor 206 and the heater 207 are electrically connected to the processor unit 4 through the wiring substrate 220. The temperature sensor 206 and the heater 207 are not limited to chips illustrated in FIG. 3, and another configuration may also be employed. Locations of the temperature sensor 206 and the heater 207 may be exchanged. Also, the temperature sensor 206 and the heater 207 may be arranged in an area in the vicinity of the objective lens frame 212 and the imaging optical system 201. That is to say, although the temperature sensor 206 and the heater 207 in this embodiment not directly but indirectly detect to heat the space in the objective lens frame 212 to be described later, of course, there is no limitation; they may also be brought into direct contact with the objective lens frame 212 to detect the temperature of the objective lens 212a to heat.

A configuration of the light source unit 3 is described with reference to FIGS. 1 and 2 again. The light source unit 3 is provided with an illumination unit 31 and an illumination controller 32.

The illumination unit 31 emits the illumination light under control of the illumination controller 32. The illumination unit 31 includes a light source 31a, a light source driver 31b, and a condenser lens 31c.

The light source 31a emits the illumination light under the control of the illumination controller 32. White illumination light generated by the light source 31a is emitted from the distal end of the insertion portion 21 to outside through the condenser lens 31c and the light guide 203. The light source 31a is realized by using a light source which generates white light such as a white LED and a xenon lamp, for example.

The light source driver 31b supplies the light source 31a with current to allow the light source 31a to emit the white illumination light under the control of the illumination controller 32.

The condenser lens 31c condenses the white illumination light emitted by the light source 31a to emit out of the light source unit 3 (light guide 203).

The illumination controller 32 controls the illumination light emitted by the illumination unit 31 by controlling the light source driver 31b to turn on/off the light source 31a.

Next, a configuration of the processor unit 4 is described. The processor unit 4 is provided with an image processing unit 41, an input unit 42, a storage unit 43, a temperature controller 44, a heater power supply unit 45, and an overall controller 46.

The image processing unit 41 executes predetermined image processing based on the electric signal output from the endoscope 2 (A/D converter 205) to generate image information for the display unit 5 to display.

The input unit 42 being an interface for inputting to the processor unit 4 by a user includes a power switch for turning on/off power, a mode switching button for switching among a shooting mode and various other modes, an illumination light switching button for switching the illumination light of the light source unit 3 and the like.

The storage unit 43 records various programs for operating the endoscope device 1 and data including various parameters required for operating the endoscope device 1 (for example, set temperature for preventing fogging on the distal end of the insertion portion 21, a threshold, and a graph indicating relationship between power and temperature difference for each ambient temperature) and the like. The storage unit 43 may also store the information regarding the endoscope 2, for example, the specific information (ID) of the endoscope 2. The storage unit 43 is realized by using a semiconductor memory such as a flash memory and a dynamic random access memory (DRAM).

The temperature controller 44 estimates the temperature difference between detected temperature based on the detection signal detected by the temperature sensor 206 and the temperature of the objective lens to calculate a power amount for driving the heater 207 based on the estimated temperature difference. The temperature controller 44 includes a temperature setting unit 441, a temperature detection unit 442, a power calculation unit 443, a state determination unit 444, and a temperature difference estimation unit 445.

The temperature setting unit 441 sets the temperature of the objective lens for preventing the fogging. The temperature setting unit 441 sets the temperature of the objective lens for preventing the fogging to the temperature stored in the storage unit 43 or target temperature calculated from the temperature difference estimated by the temperature difference estimation unit 445.

The temperature detection unit 442 calculates sensor temperature based on the detection signal detected by the temperature sensor 206. Specifically, the temperature detection unit 442 extracts the electromotive force (thermal electromotive force) from the detection signal and acquires the temperature (hereinafter, referred to as the sensor temperature) based on the electromotive force. The sensor temperature is the temperature of the area to be detected of the temperature sensor 206 (the neighboring area of the heater 207), that is to say, the temperature of an inner space (hollow space) in the objective lens frame 212 which stores (holds) the objective lens 212a.

The power calculation unit 443 calculates the power (a power value) for preventing the fogging of the objective lens supplied to the heater 207. Specifically, the power calculation unit 443 calculates the power by using a proportional integral derivative (PID) control equation and the like based on the temperature difference between the set temperature (target temperature) set by the temperature setting unit and the sensor temperature calculated by the temperature detection unit 442.

Figure 4:
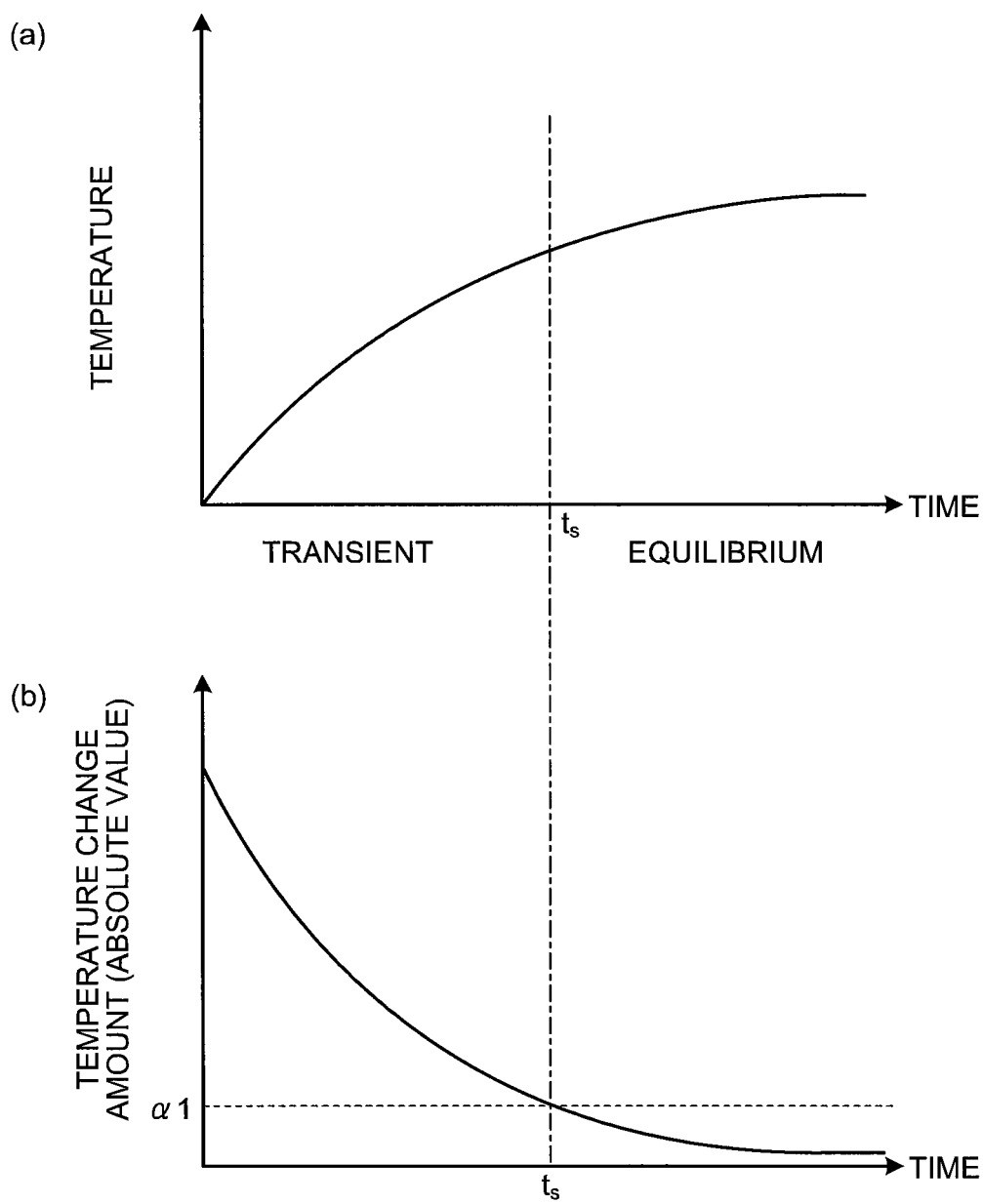
FIG. 4 is graphs illustrating a determination process performed by a state determination unit of the endoscope device according to the first embodiment of the present invention.

The state determination unit 444 determines whether a temperature state on the distal end of the endoscope 2 (heater 207) is a transient state or an equilibrium state by using the sensor temperature calculated by the temperature detection unit 442. FIG. 4 is graphs illustrating a determination process performed by the state determination unit of the endoscope device according to the first embodiment in which (a) of FIG. 4 is a graph indicating relationship between time and temperature and (b) of FIG. 4 is a graph indicating relationship between time and temperature change. The state determination unit 444 calculates a temperature change amount between the sensor temperature in a previous determination process and the currently acquired sensor temperature to determine whether the temperature change amount is not smaller than a threshold $\alpha 1$ (first threshold) set in advance. The state determination unit 444 determines that the temperature state is the transient state (second state) when the temperature change amount is not smaller than the threshold $\alpha 1$, and determines that the temperature state is the equilibrium state (first state) when the temperature change amount is smaller than the threshold $\alpha 1$. Specifically, the state determination unit 444 determines that temperature state changes from the transient state to the equilibrium state at time $t_s$ because an absolute value of the temperature change amount becomes smaller than the threshold $\alpha 1$ at time $t_s$. On the other hand, when the absolute value of the temperature change amount becomes larger than the threshold $\alpha 1$ at certain time, the state determination unit 444 determines that the temperature state changes from the equilibrium state to the transient state at that time. The transient state herein indicates a state in which there is difference between the temperature on the distal end of the insertion portion 21 and the set target temperature, and the equilibrium state indicates a state in which the temperature on the distal end of the insertion portion 21 is substantially equal to the set target temperature.

The threshold $\alpha 1$ being the value set for the temperature change amount (absolute value) is set to fall between a noise level in temperature acquisition by the temperature sensor 206 and average heating capability of the heater 207. For example, when the noise level in the temperature acquisition by the temperature sensor 206 is 0.5° C. and the average heating capability by the heater is 2.0° C./sec, the threshold $\alpha 1$ is set to be not lower than 0.5° C./sec and not higher than 2.0° C./sec. In a general temperature control system, the temperature change amount is the largest when the heating is started, the temperature change amount decreases as the temperature on the distal end of the insertion portion 21 (temperature detected by the temperature sensor 206) approaches the target temperature, and the temperature change amount drastically decreases when the temperature reaches the target temperature, so that it becomes possible to more correctly determine whether the temperature state is the transient state or the equilibrium state by setting the threshold $\alpha 1$ to a value closer to the noise level, for example, 1.0° C./sec.

The temperature difference estimation unit 445 performs an estimation process of the temperature difference when the state determination unit 444 determines that the temperature state is the equilibrium state. Specifically, the temperature difference estimation unit 445 acquires the power value input to the heater 207 from the power calculation unit 443 and estimates the temperature difference based on the relationship between the temperature difference and the power (input power) relative to the ambient temperature (usage environment temperature of the endoscope 2).

Figure 5:
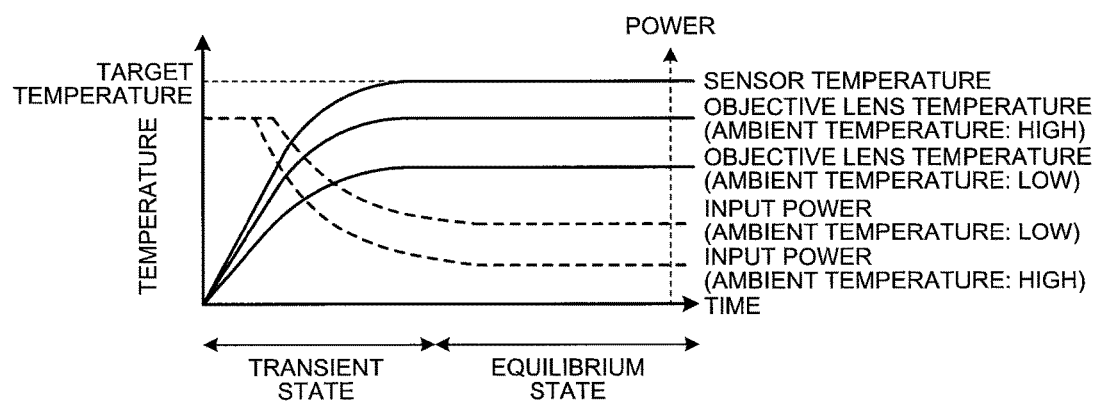
FIG. 5 is a graph illustrating temperature difference between sensor temperature by a temperature sensor and temperature of an objective lens and input power relative to ambient temperature.

FIG. 5 is a graph illustrating the temperature difference between the sensor temperature by the temperature sensor and the temperature of the objective lens and the input power relative to the ambient temperature. In a state in which the temperature change on the distal end of the insertion portion 21 is in the equilibrium state, when the target temperature of the objective lens is set to 39° C. and the ambient temperature is relatively low (for example approximately 15° C. at room temperature), a heat radiation amount from the distal end of the insertion portion 21 becomes larger, so that the temperature difference between the sensor temperature by the temperature sensor 206 and the temperature of the objective lens becomes larger and the input power to the heater for increasing the temperature up to the target temperature becomes larger. On the other hand, when the ambient temperature is relatively high (for example, approximately 25° C. at room temperature), the heat radiation amount from the distal end of the insertion portion 21 becomes smaller, so that the temperature difference between the sensor temperature by the temperature sensor 206 and the temperature of the objective lens becomes smaller and the input power to the heater 207 for increasing up to the target temperature becomes smaller.

Figure 6:
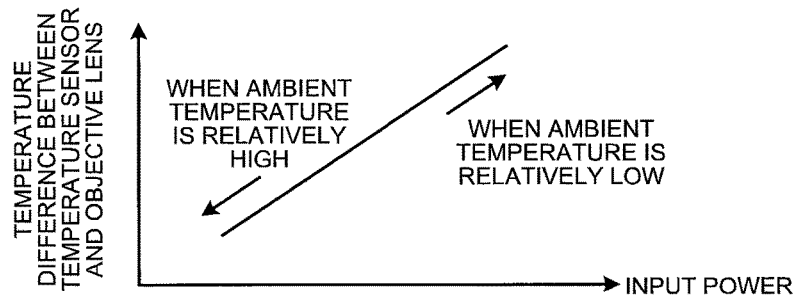
FIG. 6 is a graph illustrating relationship between the temperature difference between the sensor temperature by the temperature sensor and the temperature of the objective lens and the input power at different ambient temperatures.

FIG. 6 is a graph illustrating relationship between the temperature difference between the sensor temperature by the temperature sensor and the temperature of the objective lens and the input power at different ambient temperatures. In a state in which the temperature change on the distal end of the insertion portion 21 is in the equilibrium state, when the ambient temperature is relatively low, the input power to the heater 207 becomes larger and the temperature difference between the sensor temperature and the temperature of the objective lens becomes larger (refer to FIG. 5). On the other hand, when the ambient temperature is relatively high, the input power to the heater becomes smaller and the temperature difference between the sensor temperature and the temperature of the objective lens becomes smaller. The relationship between the temperature difference and the power relative to the ambient temperature is proportional relationship in general as illustrated in FIG. 6. Therefore, in a thermally equilibrium state, it is possible to estimate the temperature difference between the temperature sensor 206 and the objective lens by using information of the input power. That is to say, it is possible to estimate appropriate temperature difference based on the input power by acquiring the relationship between the temperature difference and the input power relative to the ambient temperature as illustrated in FIG. 6 in advance.

The temperature difference estimation unit 445 acquires the power calculated by the power calculation unit 443, the power being currently input to the heater 207 (input power), to calculate an estimated value of the temperature difference between the temperature sensor 206 and the objective lens with reference to the graph indicating the relationship between the input power and the temperature difference relative to the ambient temperature. The temperature difference estimation unit 445 may store a data function created in advance in the storage unit 43 and read the data function to calculate the temperature difference or may store the data created in advance in the storage unit 43 as matrix data and read the matrix data to calculate the temperature difference.

The heater power supply unit 45 supplies the heater 207 with the power according to the power value calculated by the power calculation unit 443.

The overall controller 46 formed of a CPU and the like performs driving control of each component including the endoscope 2 and the light source unit 3, input/output control of information to/from each component and the like. The overall controller 46 transmits setting data (for example, a pixel to be read) for imaging control recorded in the storage unit 43, a timing signal regarding imaging timing and the like to the endoscope 2 through a predetermined signal line. The overall controller 46 controls driving of the heater 207 based on the temperature difference estimated by the temperature difference estimation unit 445 by pulse width modulation (PWM) control and on/off control in addition to the PID control.

The display unit 5 is next described. The display unit 5 receives a display image signal generated by the processor unit 4 through a video cable to display the in-vivo image corresponding to the display image signal. The display unit 5 is formed of a liquid crystal, organic electro luminescence (EL) or the like.

An antifogging device 100 according to the present invention is formed at least of the imaging optical system 201, the image sensor 202, the temperature sensor 206, the heater 207, the temperature controller 44, the heater power supply unit 45, and the overall controller 46.

Figure 7:
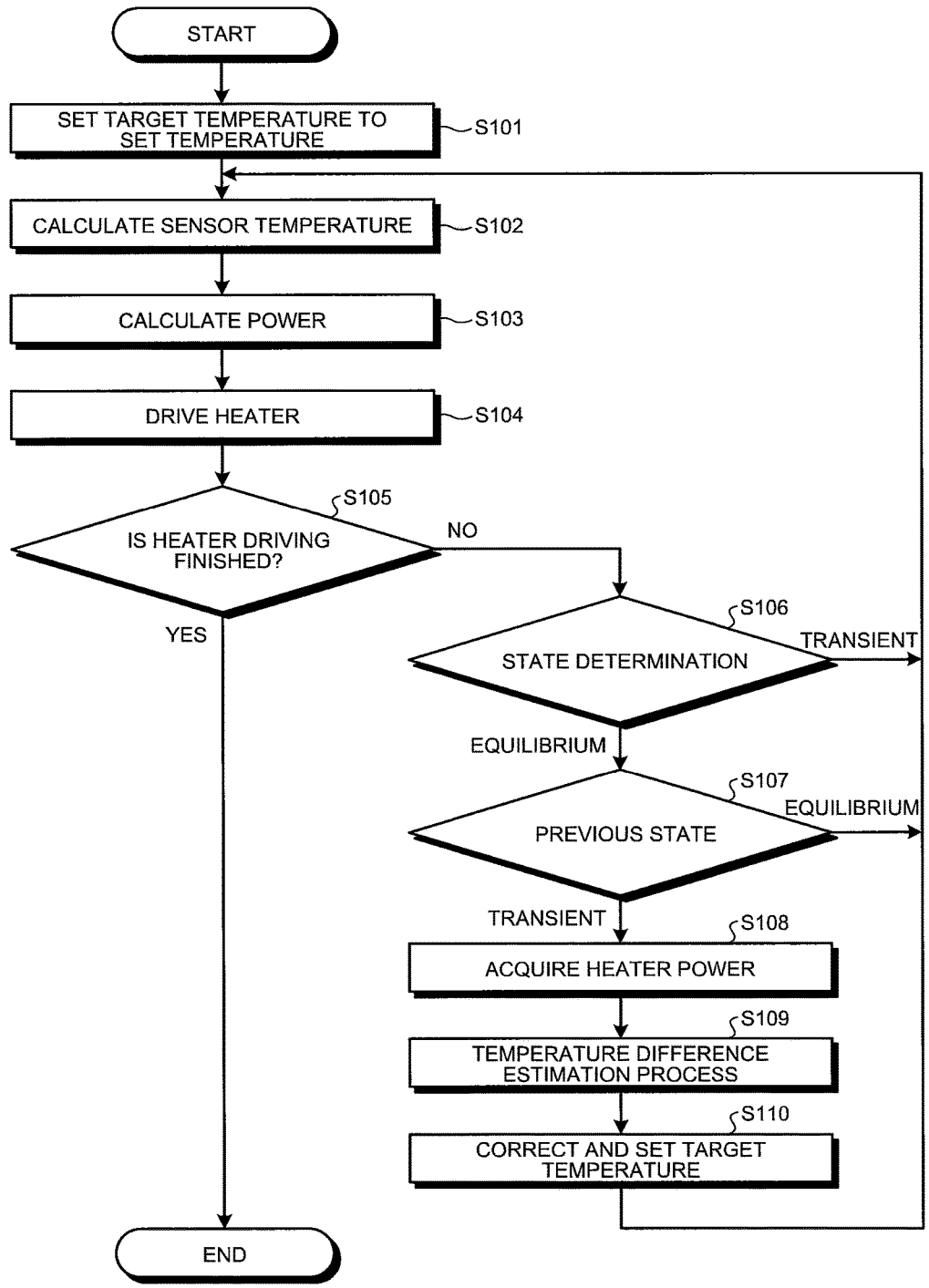
FIG. 7 is a flowchart illustrating a control process for preventing fogging performed by the endoscope device according to the first embodiment of the present invention.

FIG. 7 is a flowchart illustrating a control process for preventing the fogging performed by the endoscope device according to the first embodiment. First, the temperature setting unit 441 sets the target temperature of the objective lens to the set temperature stored in the storage unit 43 (step S101).

Thereafter, the temperature detection unit 442 calculates the sensor temperature based on the detection signal detected by the temperature sensor 206 (step S102). When the sensor temperature is acquired, the power calculation unit 443 calculates the temperature difference between the acquired sensor temperature and the set temperature set by the temperature setting unit 441, and calculates the power (power value) based on the calculated temperature difference (step S103). The power for preventing the fogging of the objective lens supplied to the heater 207 is calculated by a calculation process by the power calculation unit 443.

When the power value is output from the power calculation unit 443, the heater power supply unit 45 supplies the heater 207 with the power according to the calculated power value and performs control to drive the heater 207 (step S104). According to this, a process of heating the vicinity of the objective lens (the distal end of the insertion portion 21) by the heater 207 for preventing the fogging is performed.

Thereafter, when a command signal to finish driving the heater is output (step S105: Yes), the processor unit 4 finishes the control process. On the other hand, when the command signal to finish driving the heater is not output (step S105: No), the temperature controller 44 proceeds to step S106 to perform a state determination process of the temperature change.

At step S106, the state determination unit 444 determines whether the temperature state on the distal end of the endoscope 2 (the heater 207) is the transient state or the equilibrium state by using the sensor temperature calculated by the temperature detection unit 442 (step S106). Specifically, as described above, the state determination unit 444 calculates the temperature change amount between the sensor temperature in the previous determination process and the currently acquired sensor temperature to determine whether the temperature change amount is not smaller than the threshold α1 set in advance. The state determination unit 444 determines that the temperature state is the transient state when the temperature change amount is not smaller than the threshold α1 and determines that the temperature state is the equilibrium state when the temperature change amount is smaller than the threshold α1. When a first state determination process is performed, the temperature state is the transient state.

When the state determination unit 444 determines that the temperature state is the transient state (step S106: transient), the temperature controller 44 proceeds to step S102 to repeat the process of acquiring the sensor temperature and the subsequent processes. On the other hand, when the state determination unit 444 determines that the temperature state is the equilibrium state (step S106: equilibrium), the state determination unit 444 proceeds to step S107.

At step S107, the state determination unit 444 determines whether the previously determined state is the transient state or the equilibrium state (step S107). When the state determination unit 444 determines that the previously determined state is the equilibrium state (step S107: equilibrium), the temperature controller 44 proceeds to step S102 to repeat the process of acquiring the sensor temperature and the subsequent processes. On the other hand, when the state determination unit 444 determines that the previously determined state is the transient state (step S107: transient), the temperature controller 44 performs the estimation process of the temperature difference by the temperature difference estimation unit 445.

The temperature difference estimation unit 445 acquires the power value (power value calculated at step S103) input to the heater from the power calculation unit 443 (step S108) and performs the estimation process of the temperature difference based on the relationship between the temperature difference and the input power relative to the ambient temperature (usage environment temperature of the endoscope 2) set in advance (refer to FIG. 6) (step S109) as described above.

When the temperature difference is acquired by the estimation process by the temperature difference estimation unit 445, the temperature setting unit 441 corrects the target temperature based on the temperature difference (step S110). Specifically, the temperature setting unit 441 adds the estimated temperature difference to the currently set target temperature (for example, the temperature set at step S101) and corrects the temperature. The temperature setting unit 441 sets the corrected temperature as the target temperature. The temperature controller 44 proceeds to step S102 to repeat the above-described processes when the target temperature is reset.

By performing the control process for preventing the fogging described above, it is possible to more certainly prevent the fogging on the distal end of the endoscope 2 (insertion portion 21) by controlling the temperature by the heater with a higher degree of accuracy by estimating the temperature difference between the objective lens and the temperature sensor according to the ambient temperature, thereby correcting the target temperature.

According to the above-described first embodiment, in the heater control for preventing the fogging of the endoscope 2, the temperature difference between the objective lens and the temperature sensor is estimated according to the ambient temperature, the target temperature is corrected based on the estimated temperature difference, and the temperature on the distal end of the endoscope 2 (insertion portion 21) is controlled by the power to realize the corrected target temperature supplied to the heater, so that it is possible to correctly grasp the temperature of the optical member and certainly prevent the fogging of the optical member.

Modification of First Embodiment

Figure 8:
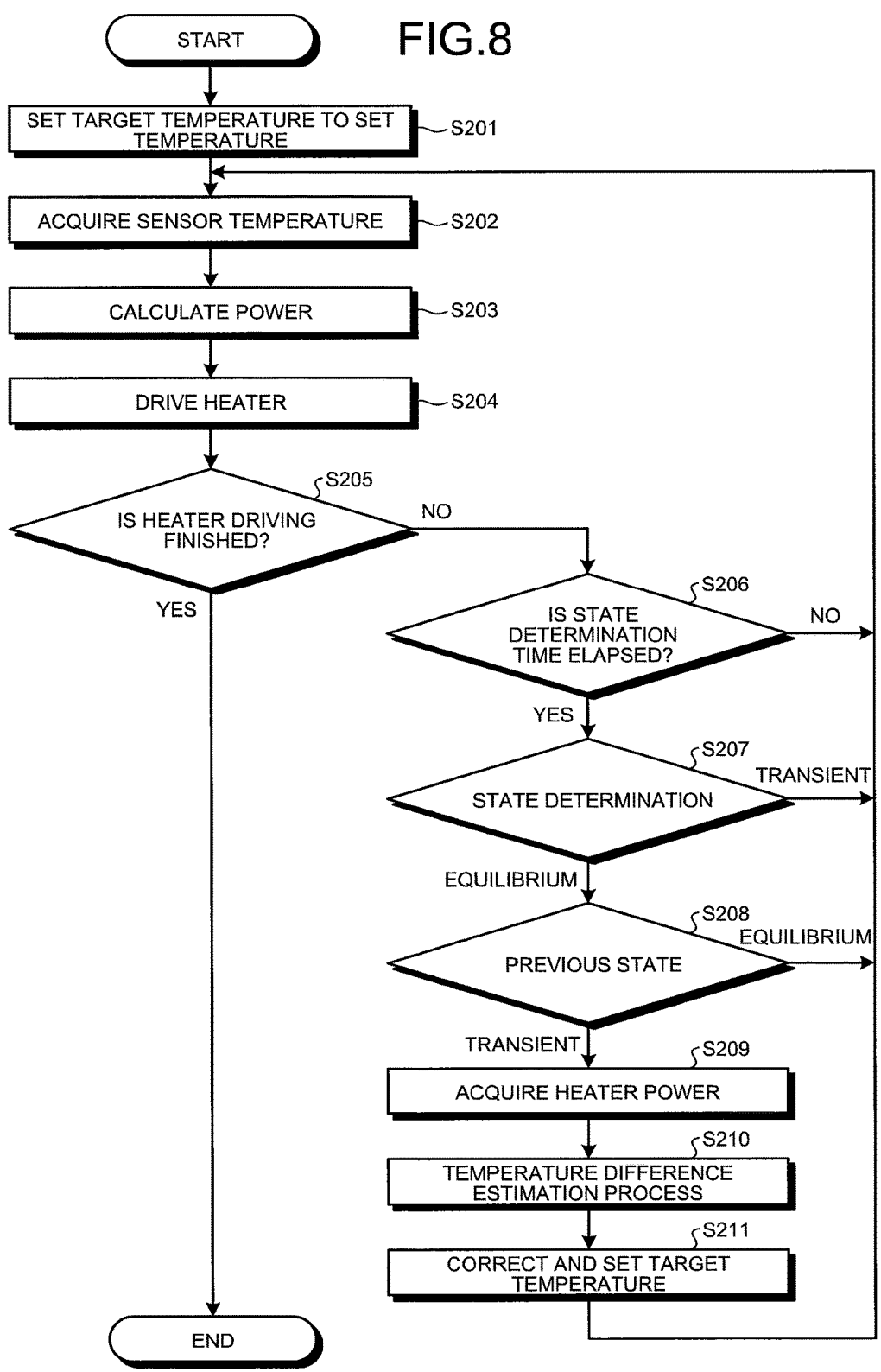
FIG. 8 is a flowchart illustrating a control process for preventing fogging performed by an endoscope device according to a modification of the first embodiment of the present invention.

FIG. 8 is a flowchart illustrating a control process for preventing fogging performed by an endoscope device according to a modification of a first embodiment. Although it is described that a determination process by a state determination unit 444 is performed every time in the above-described first embodiment, the state determination unit 444 performs the determination process when predetermined time elapses in this modification.

In the control process according to the modification, as in the first embodiment (FIG. 7), a temperature setting unit 441 sets target temperature of an objective lens to set temperature (step S201), and a temperature detection unit 442 calculates sensor temperature based on a detection signal detected by a temperature sensor 206 (step S202). Thereafter, a power calculation unit 443 calculates temperature difference between the acquired sensor temperature and the set temperature set by the temperature setting unit 441, and calculates power (a power value) based on the calculated temperature difference (step S203). When the power value is output from the power calculation unit 443, a heater power supply unit 45 controls to supply a heater 207 with the power according to the calculated power value (step S204). Thereafter, when a command signal to finish driving the heater is output (step S205: Yes), a processor unit 4 finishes the control process. On the other hand, when the command signal to finish driving the heater is not output (step S205: No), a temperature controller 44 proceeds to step S206.

At step S206, the temperature controller 44 determines whether elapsed time from a previous state determination process is longer than predetermined elapsed time. When the temperature controller 44 determines that the elapsed time from the previous state determination process is not longer than the predetermined elapsed time (step S206: No), the temperature controller 44 proceeds to step S202 to repeat the process of acquiring the sensor temperature and the subsequent processes. On the other hand, when the temperature controller 44 determines that the elapsed time from the previous state determination process is longer than the predetermined elapsed time (step S206: Yes), the temperature controller 44 proceeds to step S207 to perform a state determination process of temperature change. The elapsed time in the elapsed time determination process defines an interval at which it is determined to update the target temperature, and the elapsed time is set based on desired elapsed time, a loop count, time taking average heating capability of the heater into consideration and the like.

At step S207, the state determination unit 444 determines whether a temperature state of a distal end of an endoscope 2 is a transient state or an equilibrium state (step S207). A temperature change amount at step S207 is a change amount between the sensor temperature detected at determination reference time of the elapsed time (when starting counting time) and the currently acquired sensor temperature. When the state determination unit 444 determines that the temperature state is the transient state (step S207: transient), the temperature controller 44 proceeds to step S202 to repeat the process of acquiring the sensor temperature and the subsequent processes. On the other hand, when the state determination unit 444 determines that the temperature state is the equilibrium state (step S207: equilibrium), the state determination unit 444 proceeds to step S208.

At step S208, the state determination unit 444 determines whether the previously determined state is the transient state or the equilibrium state (step S208). When the state determination unit 444 determines that the previously determined state is the equilibrium state (step S208: equilibrium), the temperature controller 44 proceeds to step S202 to repeat the process of acquiring the sensor temperature and the subsequent processes. On the other hand, when the state determination unit 444 determines that the previously determined state is the transient state (step S208: transient), the temperature controller 44 performs an estimation process of the temperature difference by a temperature difference estimation unit 445.

The temperature difference estimation unit 445 acquires the power value (power value calculated at step S203) input to the heater from the power calculation unit 443 (step S209) and performs the estimation process of the temperature difference based on relationship between the temperature difference and the input power relative to ambient temperature set in advance (refer to FIG. 6) (step S210) as described above.

When the temperature difference is acquired by the estimation process by the temperature difference estimation unit 445, the temperature setting unit 441 corrects the target temperature based on the temperature difference (step S211). Specifically, the temperature setting unit 441 adds the estimated temperature difference to the currently set target temperature (for example, the temperature set at step S201) and corrects the temperature. The temperature setting unit 441 sets the corrected temperature as the target temperature. The temperature controller 44 proceeds to step S202 to repeat the above-described processes when the target temperature is reset.

As described above, it is possible to more appropriately perform the state determination process by determining whether the elapsed time from the previous state determination process is longer than the predetermined elapsed time and performing the state determination process according to a determination result. For example, when the determination interval is too short, there is a possibility that the temperature change amount is too small and the temperature state is not determined to be the transient state even when it is essentially wanted that the state is determined to be the transient state in terms of heat. It is possible to control the temperature (control the target temperature) with a higher degree of accuracy by setting the elapsed time.

Second Embodiment

Figure 9:
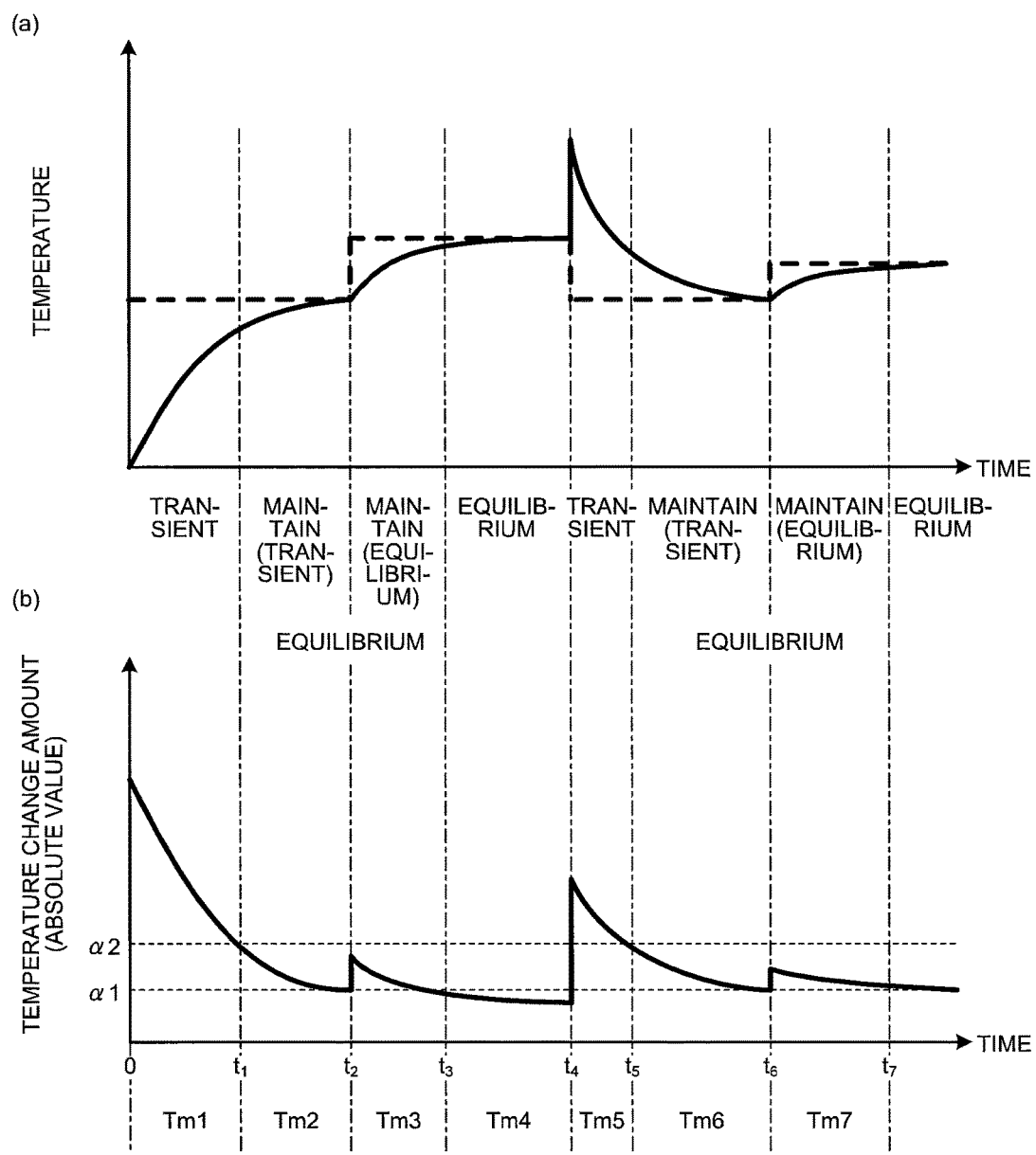
FIG. 9 is graphs illustrating a determination process performed by a state determination unit of an endoscope device according to a second embodiment of the present invention.

Next, a second embodiment of the present invention is described. FIG. 9 is graphs illustrating a determination process performed by a state determination unit of an endoscope device according to the second embodiment in which (a) of FIG. 9 is a graph indicating relationship between time and temperature and (b) of FIG. 9 is a graph indicating relationship between time and temperature change. Although it is described that a state determination unit 444 determines whether a temperature state is a transient state or an equilibrium state by using a threshold $\alpha1$ in the above-described first embodiment, in the second embodiment, two thresholds are provided and the state determination unit 444 determines which of three temperature states of the transient state, the equilibrium state, and a maintained state the temperature state is.

In the second embodiment, a storage unit 43 stores the above-described threshold $\alpha1$ (first threshold) and a threshold $\alpha2$ (second threshold). Herein, the threshold $\alpha1$ is a value set for a temperature change amount (absolute value) as described above, the value set so as to fall between a noise level in temperature acquisition by the temperature sensor 206 and average heating capability of a heater. In contrast, the threshold $\alpha2$ is a value set for the temperature change amount (absolute value) larger than the threshold α1, the value according to the temperature change amount in a supposed usage environment. For example, a value according to the temperature change amount when an insertion portion 21 is inserted into a body (body temperature) from outside the body (room temperature), a maximum value (or a minimum value or an average value) supposed in the change amount is set.

The state determination unit 444 determines that the temperature state is the transient state when the temperature change amount is not smaller than the threshold α2, and determines that the temperature state is the equilibrium state when the temperature change amount is smaller than the threshold α1. The state determination unit 444 determines that the temperature state is the maintained state when the temperature change amount falls between the thresholds α1 and α2.

Specifically, when the state determination unit 444 determines that the temperature state is the maintained state, the state determination unit 444 determines whether the previous temperature state is the transient state or the equilibrium state. When the state determination unit 444 determines that the temperature state is the maintained state and when the previous temperature state is the transient state, the state determination unit 444 resets the current state to the transient state. On the other hand, when the state determination unit 444 determines that the temperature state is the maintained state and when the previous temperature state is the equilibrium state, the state determination unit 444 resets the current state to the equilibrium state.

In FIG. 9, the temperature change amount is larger than the threshold α2 during a period Tm1 from time 0 until time $t_1$, so that the state determination unit 444 determines that the temperature state during the period Tm1 is the transient state. Since the temperature change amount is not larger than the threshold α2 and is larger than the threshold α1 and the previously determined state is the transient state during a period Tm2 from time $t_1$ before time $t_2$, the state determination unit 444 determines that the temperature state during the period Tm2 is the maintained state and thereafter sets the temperature state to the transient state.

Since the temperature change amount is not larger than the threshold α1 at time $t_2$, the state determination unit 444 determines that the temperature state at time $t_2$ is the equilibrium state. Since the temperature change amount is not larger than the threshold α2 and is larger than the threshold α1 and the previously determined state is the transient state during a period Tm3 after time $t_2$ until time $t_3$, the state determination unit 444 determines that the temperature state during the period Tm3 is the maintained state and thereafter sets the temperature state to the equilibrium state. The temperature change amount is not larger than the threshold α1 during a period Tm4 from time $t_3$ before time $t_4$, so that the state determination unit 444 determines that the temperature state during the period Tm4 is the equilibrium state.

Since the temperature change amount is larger than the threshold α2 at time $t_4$, the state determination unit 444 determines that the temperature state at time $t_4$ is the transient state. At time $t_4$, the temperature state transits from the equilibrium state to the transient state. In other words, the temperature change amount drastically changes from a value not larger than the threshold α1 to a value larger than the threshold α2. Regarding the drastic change in the temperature change amount at time $t_4$, environment temperature changes from 20° C. to 37° C. when the insertion portion 21 is inserted into the body from outside the body, for example, so that a detected temperature by the temperature sensor 206 also widely increases. The drastic change might occur in the temperature change amount due to such change in the environment temperature. Thereafter, the temperature change amount is larger than the threshold α2 during a period Tm5 from time $t_4$ until time $t_5$, so that the state determination unit 444 determines that the temperature state during the period Tm5 is the transient state.

Since the temperature change amount is not larger than the threshold α2 and is larger than the threshold α1 and the previously determined state is the transient state during a period Tm6 from time $t_5$ before time $t_6$, the state determination unit 444 determines that the temperature state during the period Tm6 is the maintained state and thereafter sets the temperature state to the transient state.

Since the temperature change amount is not larger than the threshold α1 at time $t_6$, the state determination unit 444 determines that the temperature state at time $t_6$ is the equilibrium state. Since the temperature change amount is not larger than the threshold α2 and is larger than the threshold α1 and the previously determined state is the equilibrium state during a period Tm7 after time $t_6$ until time $t_7$, the state determination unit 444 determines that the temperature state during the period Tm7 is the maintained state and thereafter sets the temperature state to the equilibrium state.

In this manner, the state determination unit 444 determines which of the transient state, the equilibrium state, and the maintained state the temperature state of a distal end of the insertion portion 21 (heater 207) is, and when determining that the temperature state is the maintained state, the state determination unit 444 determines whether to maintain the transient state or maintain the equilibrium state by using the temperature change amount, the thresholds α1 and α2, and the previous temperature state.

Figure 10:
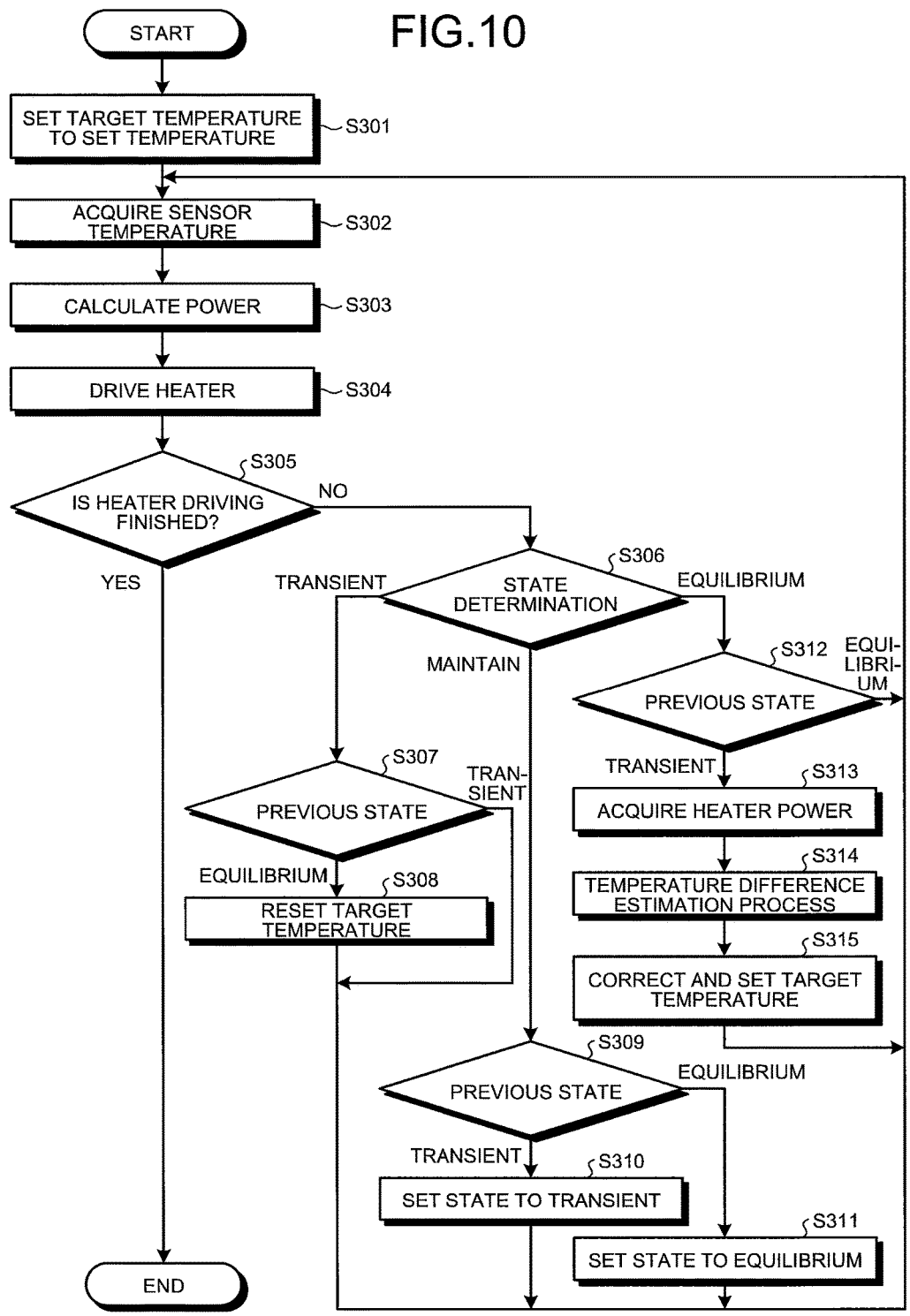
FIG. 10 is a flowchart illustrating a control process for preventing fogging performed by the endoscope device according to the second embodiment of the present invention.

FIG. 10 is a flowchart illustrating a control process for preventing fogging performed by the endoscope device according to the second embodiment. In the control process according to the second embodiment, as in the first embodiment (FIG. 7), a temperature setting unit 441 sets target temperature of an objective lens to set temperature (step S301), and a temperature detection unit 442 calculates sensor temperature based on a detection signal detected by the temperature sensor 206 (step S302). Thereafter, a power calculation unit 443 calculates temperature difference between the acquired sensor temperature and the set temperature set by the temperature setting unit 441, and calculates power (a power value) based on the calculated temperature difference (step S303). When the power value is output from the power calculation unit 443, a heater power supply unit 45 controls to supply a heater 207 with the power according to the calculated power value (step S304). Thereafter, when a command signal to finish driving the heater is output (step S305: Yes), a processor unit 4 finishes the control process. On the other hand, when the command signal to finish driving the heater is not output (step S305: No), a temperature controller 44 proceeds to step S306 to perform a state determination process of the temperature change.

At step S306, the state determination unit 444 determines whether the temperature state of a distal end of an endoscope 2 is the transient state, the maintained state, or the equilibrium state (step S306). The state determination unit 444 calculates the temperature change amount between the sensor temperature in a previous determination process and the currently acquired sensor temperature to determine whether the temperature change amount is not smaller than the threshold α1 set in advance or not smaller than the threshold α2.

When the state determination unit 444 determines that the temperature state is the transient state (for example, the periods Tm1 and Tm5 in FIG. 9) (step S306: transient), the temperature controller 44 proceeds to step S307. At step S307, the state determination unit 444 determines whether the previously determined state is the transient state or the equilibrium state (step S307). When the state determination unit 444 determines that the previously determined state is the transient state (step S307: transient), the temperature controller 44 proceeds to step S302 to repeat the process of acquiring the sensor temperature and the subsequent processes. On the other hand, when the state determination unit 444 determines that the previously determined state is the equilibrium state (step S307: equilibrium), the temperature controller 44 proceeds to step S308. At step S308, the temperature setting unit 441 sets (resets) the target temperature to the set temperature stored in the storage unit 43 (step S308). After the target temperature is reset, the temperature controller 44 proceeds to step S302 to repeat the process of acquiring the sensor temperature and the subsequent processes.

On the other hand, when the state determination unit 444 determines that the temperature state is the maintained state (for example, the periods Tm2, Tm3, Tm6, and Tm7 in FIG. 9) (step S306: maintain), the temperature controller 44 proceeds to step S309. At step S309, the state determination unit 444 determines whether the previously determined state is the transient state or the equilibrium state (step S309). When the state determination unit 444 determines that the previously determined state is the transient state (for example, the periods Tm2 and Tm6 in FIG. 9) (step S309: transient), the temperature controller 44 proceeds to step S310 and sets the determined state to the transient state (step S310). After the determined state is set to the transient state, the temperature controller 44 proceeds to step S302 to repeat the process of acquiring the sensor temperature and the subsequent processes. On the other hand, when the state determination unit 444 determines that the previously determined state is the equilibrium state (for example, the periods Tm3 and Tm7 in FIG. 9) (step S309: equilibrium), the temperature controller 44 proceeds to step S311 and sets the determined state to the equilibrium state (step S311). After the determined state is set to the equilibrium state, the temperature controller 44 proceeds to step S302 to repeat the process of acquiring the sensor temperature and the subsequent processes.

When the state determination unit 444 determines that the temperature state is the equilibrium state (for example, the period Tm4 and times $t_2$ and $t_6$ in FIG. 9) (step S306: equilibrium), the temperature controller 44 proceeds to step S312. At step S312, the state determination unit 444 determines whether the previously determined state is the transient state or the equilibrium state (step S312). When the state determination unit 444 determines that the previously determined state is the equilibrium state (step S312: equilibrium), the temperature controller 44 proceeds to step S302 to repeat the process of acquiring the sensor temperature and the subsequent processes. On the other hand, when the state determination unit 444 determines that the previously determined state is the transient state (step S312: transient), the temperature controller 44 performs an estimation process of the temperature difference by the temperature difference estimation unit 445.

The temperature difference estimation unit 445 acquires the power value (power value calculated at step S303) input to the heater from the power calculation unit 443 (step S313) and performs the estimation process of the temperature difference based on relationship between the temperature difference and the input power relative to ambient temperature set in advance (refer to FIG. 6) (step S314) as described above.

When the temperature difference is acquired by the estimation process by the temperature difference estimation unit 445, the temperature setting unit 441 corrects the target temperature based on the temperature difference (step S315). Specifically, the temperature setting unit 441 adds the estimated temperature difference to the currently set target temperature (for example, the temperature set at step S301) and corrects the temperature. The temperature setting unit 441 sets the corrected temperature as the target temperature. The temperature controller 44 proceeds to step S302 to repeat the above-described processes when the target temperature is reset.

According to the above-described second embodiment, in heater control for preventing the fogging of the endoscope 2, the temperature difference between the objective lens and the temperature sensor is estimated according to the ambient temperature, the target temperature is corrected based on the estimated temperature difference, and the power to realize the corrected target temperature is supplied to the heater, thereby controlling the temperature of the distal end of the endoscope 2 (insertion portion 21), so that it is possible to correctly grasp the temperature of an optical member and certainly prevent the fogging of the optical member.

According to the above-described second embodiment, the state determination unit 444 defines the transient state, the equilibrium state, and the maintained state being the state between the transient state and the equilibrium state by the threshold α1 set to fall between the noise level in the temperature acquisition by the temperature sensor 206 and the average heating capability of the heater and the threshold α2 being the value set for the temperature change amount (absolute value), the value according to the temperature change amount in the supposed usage environment and takes over the previous state when the temperature state is determined to be the maintained state, so that erroneous operation due to minute variation occurring when the target temperature is corrected may be prevented.

Modification of Second Embodiment

Figure 11:
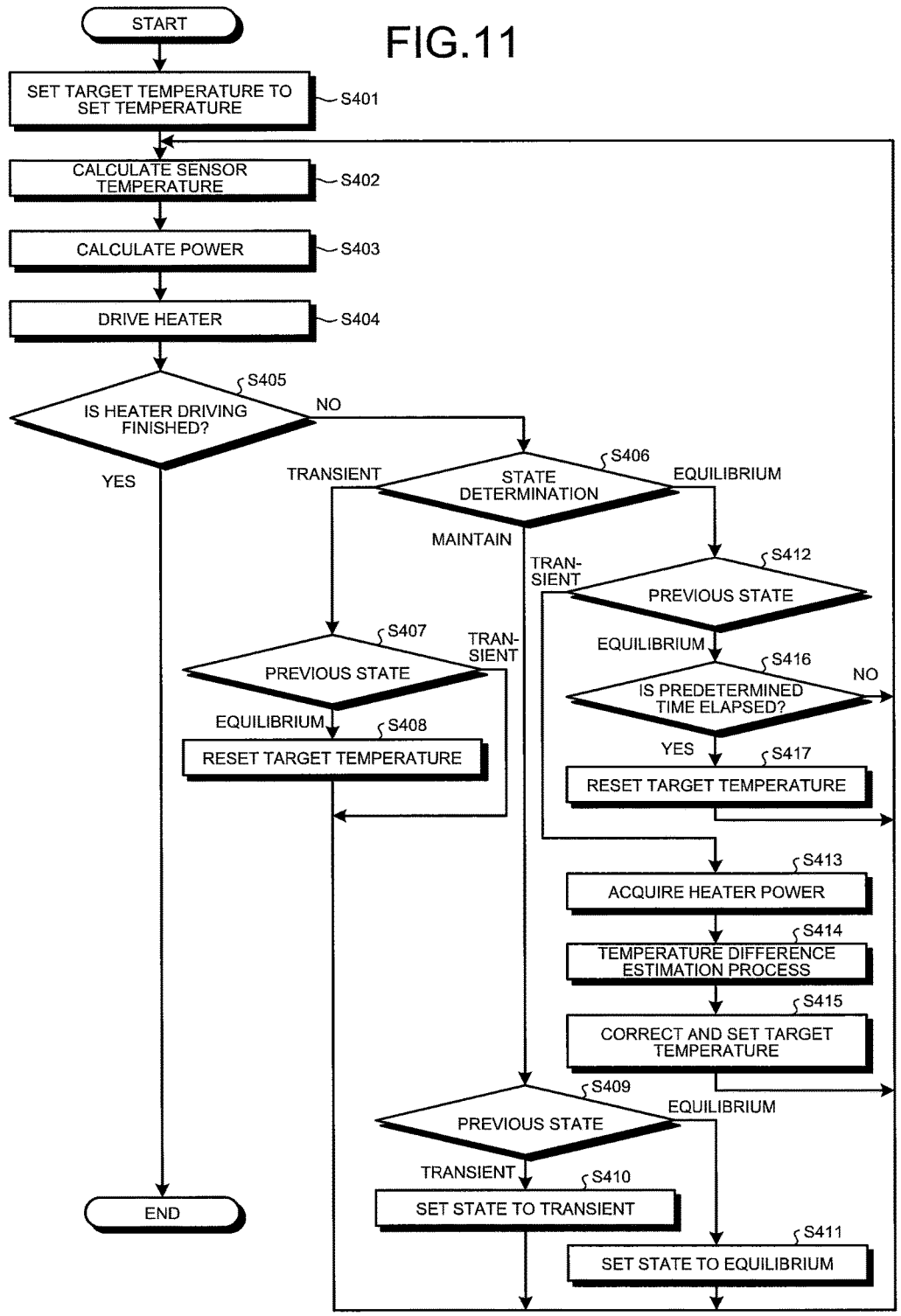
FIG. 11 is a flowchart illustrating a control process for preventing fogging performed by an endoscope device according to a modification of the second embodiment of the present invention.

FIG. 11 is a flowchart illustrating a control process for preventing fogging performed by an endoscope device according to a modification of a second embodiment. Different from the control process according to the above-described second embodiment, in this modification, if predetermined time has elapsed, target temperature is corrected even when a current state and a previously determined state are equilibrium states.

In the control process according to this modification, processes similar to those from step S301 to step S312 of the above-described second embodiment (FIG. 10) are performed (steps S401 to S412).

Herein, when a state determination unit 444 determines that the previously determined state is a transient state at step S412 (step S412: transient), the temperature controller 44 performs an estimation process of temperature difference by a temperature difference estimation unit 445. The temperature difference estimation unit 445 acquires a power value (power value calculated at step S403) input to a heater from a power calculation unit 443 (step S413) and performs the estimation process of the temperature difference based on relationship between the temperature difference and the input power relative to ambient temperature set in advance (refer to FIG. 6) (step S414) as described above.

When the temperature difference is acquired by the estimation process by the temperature difference estimation unit 445, a temperature setting unit 441 corrects target temperature based on the temperature difference (step S415). Specifically, the temperature setting unit 441 adds the estimated temperature difference to the currently set target temperature (for example, the temperature set at step S401 and corrected temperature) and corrects the temperature. The temperature setting unit 441 sets the corrected temperature as the target temperature. The temperature controller 44 proceeds to step S402 to repeat the above-described processes when the target temperature is reset.

On the other hand, when the state determination unit 444 determines that the previously determined state is the equilibrium state (step S412: equilibrium), the temperature controller 44 proceeds to step S416. At step S416, the temperature controller 44 determines whether elapsed time during which the equilibrium state is maintained from reference time at which the temperature state is first determined to be the equilibrium state becomes longer than predetermined elapsed time (step S416). When the temperature controller 44 determines that the elapsed time from the previous state determination process is not longer than the predetermined elapsed time (step S416: No), the temperature controller 44 proceeds to step S402 to repeat the process of acquiring the sensor temperature and the subsequent processes. On the other hand, when the temperature controller 44 determines that the elapsed time from the previous state determination process is longer than the predetermined elapsed time (step S416: Yes), the temperature controller 44 proceeds to step S417 to perform a reset process of the target temperature (step S417). The elapsed time in the elapsed time determination process also defines an interval at which it is determined to update the target temperature as described above, and the elapsed time is set based on desired elapsed time, a loop count and the like.

As described above, when the ambient temperature gradually changes, for example, temperature change at the time of state determination does not occur, so that there is a possibility that the temperature state is always determined to be the equilibrium state and necessary correction is not performed. Therefore, it is possible to more appropriately perform the state determination process by determining whether the elapsed time from the previous state determination process is longer than the predetermined elapsed time when the equilibrium state continues for a long time and performing the reset process of the target temperature according to the determination result.

In the modification of the second embodiment, when the ambient temperature gradually changes, the temperature change does not occur but the power input to a heater 207 changes. Therefore, it is also possible that a threshold α3 is defined for a change amount (absolute value) of the power input to the heater 207 in advance and the state determination unit 444 performs the reset process of the target temperature when the change amount of the power input to the heater 207 changes so as to be not smaller than the threshold α3 at an arbitrary time interval longer than the predetermined elapsed time when the temperature state of a distal end of an insertion portion 21 is the equilibrium state. In this manner, it is possible to correct the target set temperature again by using a parameter different from the temperature change amount.

Although the endoscope 2 is a medical rigid scope in the first and second embodiments, a flexible medical endoscope or an industrial endoscope may also be employed. It is possible to prevent the fogging of the distal end of the insertion portion 21 by performing the above-described control process for prevent the fogging on the endoscope by setting the temperature and threshold according to the usage environment and the like.

Although the state determination unit 444 calculates the temperature change amount between the sensor temperature in the previous determination process and the currently acquired sensor temperature and determines whether the temperature state is the transient state or the equilibrium state based on the temperature change amount in the first and second embodiments, it is also possible to determine whether the temperature state is the transient state or the equilibrium state based on the change amount of the power input to the heater 207.

According to some embodiments, it is possible to correctly grasp the temperature of the optical member and surely prevent the fogging of the optical member.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An antifogging device comprising:
    an optical system having one or more optical members including at least an objective lens;
    a hollow casing in which the optical system is stored;
    a heater configured to generate heat according to a supplied power to heat a hollow space in the casing;
    a temperature sensor configured to detect a temperature of the hollow space;
    a temperature controller configured to estimate a temperature difference between the temperature detected by the temperature sensor and a temperature of the one or more optical members, based on a power value of the supplied power; and
    an overall controller configured to control the heater based on the temperature difference estimated by the temperature controller;
    wherein
    the temperature controller is configured to:
        set a target temperature of the one or more optical members to a first temperature;
        correct the first temperature based on the estimated temperature difference to acquire a corrected first temperature as a second temperature; and
        set the second temperature as the target temperature.

2. The antifogging device according to claim 1, wherein
    the temperature controller is configured to determine whether a temperature state of the heater is a first state or a second state, the first state and the second state being set according to an amount of change in the temperature detected by the temperature sensor at different points in time, wherein
    the first state is smaller in the amount of change than the second state, and
    the temperature controller is configured to estimate the temperature difference when the temperature state is the first state.

3. The antifogging device according to claim 2, wherein the temperature controller is configured to set the target temperature to the first temperature when the temperature state transits from the first state to the second state.

4. The antifogging device according to claim 2, wherein the temperature controller is configured to determine whether the amount of change is not smaller than a first threshold, the temperature controller is configured to determine that the temperature state is the second state when the amount of change is not smaller than the first threshold, and the temperature controller is configured to determine that the temperature state is the first state when the amount of change is smaller than the first threshold.

5. The antifogging device according to claim 4, wherein the temperature controller is configured to determine that a current temperature state is maintained in a previous temperature state when the amount of change is not smaller than the first threshold and is not larger than a second threshold larger than the first threshold.

6. The antifogging device according to claim 5, wherein the temperature controller is configured to set the target temperature to the first temperature when an elapsed time during which the first state is maintained is longer than a predetermined elapsed time.

7. The antifogging device according to claim 2, wherein the temperature controller is configured to perform a determination process of the temperature state when a predetermined time has elapsed from a previous determination process.

8. An endoscope device comprising:

an insertion portion having an imaging optical system including one or more optical members including at least an objective lens, an image sensor configured to capture a formed image transmitted through the imaging optical system, a hollow casing in which the imaging optical system and the image sensor are stored, a heater configured to generate heat according to a supplied power to heat a hollow space in the casing, and a temperature sensor configured to detect a temperature of the hollow space;

a temperature controller configured to estimate, based on a power value of the supplied power, a temperature difference between the temperature detected by the temperature sensor and a temperature of an optical member among the one or more optical members of the imaging optical system, the optical member being located on a most distal end of the insertion portion; and an overall controller configured to control the heater based on the temperature difference estimated by the temperature controller;

wherein the temperature controller is configured to:

set a target temperature of the one or more optical members to a first temperature;

correct the first temperature based on the estimated temperature difference to acquire a corrected first temperature as a second temperature; and set the second temperature as the target temperature.

* * * * *